United States Patent [19]
Schneider et al.

[11] Patent Number: 5,861,254
[45] Date of Patent: Jan. 19, 1999

[54] FLOW CELL SELEX

[75] Inventors: Daniel J. Schneider, Broomfield; Rebecca Vanderslice; Larry Gold, both of Boulder, all of Colo.

[73] Assignee: NeXstar Pharmaceuticals, Inc., Boulder, Colo.

[21] Appl. No.: 792,075

[22] Filed: Jan. 31, 1997

[51] Int. Cl.$^6$ .............................. C12P 19/34; C12Q 1/68; C07H 21/02; G01N 21/01
[52] U.S. Cl. ........................ 435/6; 435/91.2; 536/25.4; 935/77; 935/78; 422/88.11
[58] Field of Search .................. 435/6, 91.2; 536/25.4; 935/77, 78; 422/88.11

[56] References Cited

U.S. PATENT DOCUMENTS

| | | | |
|---|---|---|---|
| 5,459,015 | 10/1995 | Janjic et al. | 435/6 |
| 5,472,841 | 12/1995 | Jayasena et al. | 435/6 |
| 5,476,766 | 12/1995 | Gold et al. | 435/6 |
| 5,492,840 | 2/1996 | Malmqvist et al. | 436/518 |
| 5,496,938 | 3/1996 | Gold et al. | 536/22.1 |
| 5,503,978 | 4/1996 | Schneider et al. | 435/6 |
| 5,527,894 | 6/1996 | Gold et al. | 536/22.1 |
| 5,543,293 | 8/1996 | Gold et al. | 435/6 |
| 5,567,588 | 10/1996 | Gold et al. | 435/6 |
| 5,580,737 | 12/1996 | Polisky et al. | 435/6 |
| 5,587,468 | 12/1996 | Allen et al. | 536/22.1 |
| 5,595,877 | 1/1997 | Gold et al. | 435/6 |
| 5,620,850 | 4/1997 | Bamdad et al. | 530/300 |

FOREIGN PATENT DOCUMENTS

| | | |
|---|---|---|
| 2 183 661 | 6/1985 | United Kingdom . |
| WO 89/06694 | 7/1989 | WIPO . |
| WO 91/19813 | 12/1991 | WIPO . |
| WO 92/06380 | 4/1992 | WIPO . |
| WO 92/14843 | 9/1992 | WIPO . |
| WO 93/05182 | 3/1993 | WIPO . |

OTHER PUBLICATIONS

Cheskis et al. (1996) Biochemistry 35:3309.
Ellington & Szostak (1990) Abstracts of papers presented at the 1990 meeting on RNA Processing, Cold Spring Harbor Laboratory, Cold Spring Harbor, NY, p. 84.
Fisher et al (1994) Protein Science 3:257.
Joyce (1989) Gene 82:83.
Joyce & Inoue (1989) Nucleic Acids Research 17:711.
Karlsson (1994) Analytical Biochemistry 221:142.
Karlsson et al. (1991) J. of Immunological Methods 145:229.
Kinzler & Vogelstein (1989) Nucleic Acids Research 17:3645.
Kramer et al. (1974) J. Mol. Biol. 89:719.
Levisohn & Spiegelman (1969) Proc. Natl. Acad. Sci. USA 63:805.
Levisohn & Spiegelman (1968) Proc. Natl. Acad. Sci. USA 60:866.

(List continued on next page.)

Primary Examiner—Stephanie W. Zitomer
Attorney, Agent, or Firm—Swanson & Bratschun LLC

[57] ABSTRACT

Described herein are methods for improved partitioning between high and low affinity nucleic acid ligands identified through the SELEX method, termed Flow Cell SELEX. The Flow Cell SELEX method achieves partitioning between high and low affinity nucleic acid ligands using surface plasmon resonance technology. The method of the present invention presents a new and powerful approach to select nucleic acid ligands by providing a partitioning method which 1) enables a significant increase in the efficiency of partitioning from traditional partitioning methods used in SELEX, 2) allows for real time monitoring of the partitioning of the high affinity ligands from the low affinity ligands 3) allows for the ability to select for a nucleic acid ligand having specific kinetic properties, 4) does not rely on radiolabeling or other means of tagging for detection, and 5) allows for use of smaller amounts of target than in traditional methods of SELEX.

13 Claims, 5 Drawing Sheets

OTHER PUBLICATIONS

Oliphant et al. (1989) Mol. Cell. Biol. 9:2944.
Oliphant & Struhl (1988) Nucleic Acids Research 16:7673.
Oliphant & Struhl (1987) Methods in Enzymology 155:568.
Oliphant et al. (1986) Gene 44:177.
Robertson & Joyce (1990) Nature 344:467.
Thiesen & Bach (1990) Nucleic Acids Research 18:3203.

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear     ( i i ) MOLECULE TYPE: RNA     ( i x ) FEATURE:
        ( D ) OTHER INFORMATION: All C s are 2'-F cytosine     ( i x ) FEATURE:
        ( D ) OTHER INFORMATION: All U s are 2'-F uracil     ( x i ) SEQUENCE DESCRIPTION: SEQ ID NO: 1:

```
TCGGGCGGAA   TTCAGGNNNN   NNNNNNNNN   NNNNNNNNN   NNNNNCCGC            50
ATCGTCCTCC   C                                                         61
```

( 2 ) INFORMATION FOR SEQ ID NO: 2:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear     ( i i ) MOLECULE TYPE: RNA     ( i x ) FEATURE:
        ( D ) OTHER INFORMATION: All C s are 2'-F cytosine     ( i x ) FEATURE:
        ( D ) OTHER INFORMATION: All U s are 2'-F uracil     ( x i ) SEQUENCE DESCRIPTION: SEQ ID NO: 2:

```
TAATACGACT   CACTATAGGG   AGGACGATGC   GG                              32
```

( 2 ) INFORMATION FOR SEQ ID NO: 3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( i i ) MOLECULE TYPE: RNA     ( i x ) FEATURE:
        ( D ) OTHER INFORMATION: All C s are 2'-F cytosine     ( i x ) FEATURE:
        ( D ) OTHER INFORMATION: All U s are 2'-F uracil     ( x i ) SEQUENCE DESCRIPTION: SEQ ID NO: 3:

```
TCGGGCGGAA   TTCAGG                                                    16
```

( 2 ) INFORMATION FOR SEQ ID NO: 4:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear (  i  i  ) MOLECULE TYPE: RNA (  i  x  ) FEATURE:
    ( D ) OTHER INFORMATION: All C s are 2'-F cytosine (  i  x  ) FEATURE:
    ( D ) OTHER INFORMATION: All U s are 2'-F uracil (  x  i  ) SEQUENCE DESCRIPTION: SEQ ID NO: 4:

GACCAAGCTT AGCCATGATA TTTCCATGGA AA           32

( 2 ) INFORMATION FOR SEQ ID NO: 5:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear (  i  i  ) MOLECULE TYPE: RNA (  i  x  ) FEATURE:
    ( D ) OTHER INFORMATION: All C s are 2'-F cytosine (  i  x  ) FEATURE:
    ( D ) OTHER INFORMATION: All U s are 2'-F uracil (  x  i  ) SEQUENCE DESCRIPTION: SEQ ID NO: 5:

GCCAGGATCC ACTTACCTGT GTTATAATCA CCCTCCTTAA TC        42

( 2 ) INFORMATION FOR SEQ ID NO: 6:

( i ) SEQUENCE CHARACTERISTICS:
    ( A ) LENGTH: 70 base pairs
    ( B ) TYPE: nucleic acid
    ( C ) STRANDEDNESS: single
    ( D ) TOPOLOGY: linear (  i  i  ) MOLECULE TYPE: RNA (  i  x  ) FEATURE:
    ( D ) OTHER INFORMATION: All C s are 2'-F cytosine (  i  x  ) FEATURE:
    ( D ) OTHER INFORMATION: All U s are 2'-F uracil (  x  i  ) SEQUENCE DESCRIPTION: SEQ ID NO: 6:

GGGAGGACGA UGCGGUGCUA UUCUUAAGCG GCGUGUUUUU CAAGCCAAUA      50

UCAUCAGACG ACUCGCCCGA      70

FLOW CELL SELEX

FIELD OF THE INVENTION

This invention relates to the field of nucleic acids, specifically to a method of identifying nucleic acid ligands to a target. The method disclosed herein is a modification of the SELEX technology, an acronym for Systematic Evolution of Ligands by EXponential enrichment. Specifically, the method disclosed herein includes the selection of nucleic acid ligands using surface plasmon resonance technology. The SELEX method described herein, termed Flow Cell SELEX, allows more efficient method of partitioning between high and low affinity nucleic acid ligands to a target and a method of monitoring this partitioning. The method disclosed presents a new and powerful approach to select nucleic acid ligands to a desired target by providing a partitioning method which 1) enables a significant increase in the efficiency of partitioning from traditional partitioning methods used in SELEX, 2) allows for real time monitoring of the partitioning of the high affinity ligands from the low affinity ligands, 3) allows for the ability to select for a nucleic acid ligand having specific kinetic properties, 4) does not rely on radiolabeling or other means of tagging for detection, 5) allows for use of smaller amounts of target than in traditional methods of SELEX, and 6) allows for the use of physiological flow conditions in identifying a nucleic acid ligand.

The high affinity nucleic acid ligands identified by Flow Cell SELEX are useful for a number of purposes, for example, as diagnostic or therapeutic agents or in assay methods, or inhibitors or enhancers of target function. In addition, the nucleic acid ligands identified can have catalytic activity.

BACKGROUND OF THE INVENTION

The SELEX method (hereinafter termed SELEX), described in U.S. patent application Ser. No. 07/536,428, filed Jun. 11, 1990, entitled Systematic Evolution of Ligands By Exponential Enrichment, now abandoned, U.S. patent application Ser. No. 07/714,131, filed Jun. 10, 1991, entitled Nucleic Acid Ligands, now U.S. Pat. No. 5,475,096, and U.S. patent application Ser. No. 07/931,473, filed Aug. 17, 1992, entitled Method for Indentifying Nucleic Acid Ligands, now U.S. Pat. No. 5,270,163, all of which are herein specifically incorporated by reference, provides a class of products which are nucleic acid molecules, each having a unique sequence, each of which has the property of binding specifically to a desired target compound or molecule. Each nucleic acid molecule is a specific ligand of a given target compound or molecule. SELEX is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size can serve as targets.

The SELEX method involves selection from a mixture of candidates and step-wise iterations of structural improvement, using the same general selection theme, to achieve virtually any desired criterion of binding affinity and selectivity. Starting from a mixture of nucleic acids, preferably comprising a segment of randomized sequence, the method, termed SELEX herein, includes steps of contacting the mixture with the target under conditions favorable for binding, partitioning unbound nucleic acids from those nucleic acids which have bound to target molecules, dissociating the nucleic acid-target pairs, amplifying the nucleic acids dissociated from the nucleic acid-target pairs to yield a ligand-enriched mixture of nucleic acids, then reiterating the steps of binding, partitioning, dissociating and amplifying through as many cycles as desired.

While not bound by a theory of preparation, SELEX is based on the inventors' insight that within a nucleic acid mixture containing a large number of possible sequences and structures there is a wide range of binding affinities for a given target. A nucleic acid mixture comprising, for example a 20 nucleotide randomized segment can have $4^{20}$ candidate possibilities. Those which have the higher affinity constants for the target are most likely to bind. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands.

Cycles of selection and amplification are repeated until a desired goal is achieved. In the most general case, selection/amplification is continued until no significant improvement in binding strength is achieved on repetition of the cycle. The method may be used to sample as many as about $10^{18}$ different nucleic acid species. The nucleic acids of the test mixture preferably include a randomized sequence portion as well as conserved sequences necessary for efficient amplification. Nucleic acid sequence variants can be produced in a number of ways including synthesis of randomized nucleic acid sequences and size selection from randomly cleaved cellular nucleic acids. The variable sequence portion may contain fully or partially random sequence; it may also contain subportions of conserved sequence incorporated with randomized sequence. Sequence variation in test nucleic acids can be introduced or increased by mutagenesis before or during the selection/amplification iterations.

Current partitioning methods typically used in SELEX rely on a partitioning matrix. High affinity oligonucleotides may be separated in a chromatographic-type process, by binding to nitrocellulose filters, liquid-liquid partition, filtration gel retardation, and density gradient centrifugation.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," abandoned in favor of U.S. patent application Ser. No. 08/198,670, now U.S. Pat. No. 5,707,796 describes the use of SELEX in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands," describes a SELEX based method for selecting nucleic acid ligands containing photoreactive groups capable of binding and/or photo-crosslinking and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," now abandoned in favor of U.S. patent application Ser. No. 08/443,957, now U.S. Pat. No. 5,580,737 describes a method for identifying highly specific nucleic acid ligands able to discriminate between closely related molecules, which can be non-peptidic, termed Counter-SELEX. U.S. patent application Ser. No. 08/143,564, filed Oct. 25, 1993, entitled "Systematic Evolution of Ligands by Exponential Enrichment: Solution SELEX," abandoned in favor of U.S.

patent application Ser. No. 08/461,069, now U.S. Pat. No. 5,567,588, describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled "High Affinity Nucleic Acid Ligands containing Modified Nucleotides", abandoned in favor of U.S. application Ser. No. 08/430,709, now U.S. Pat. No. 5,660,985 that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2'-Modified Nucleosides by Intramolecular Nucleophilic Displacement", describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX", now U.S. Pat. No. 5,637,459, and U.S. patent application Ser. No. 08/234,997, filed Apr. 28, 1994, entitled "Systematic Evolution of Ligands by Exponential Enrichment: Blended SELEX," now U.S. Pat. No. 5,683,687, respectively. These applications allow the combination of the broad array of shapes and other properties, and the efficient amplification and replication properties, of oligonucleotides with the desirable properties of other molecules.

The SELEX method encompasses complexes of oligonucleotides. U.S. patent application Ser. No. 08/434,465, filed May 4, 1995 entitled "Nucleic Acid Ligand Complexes", describes a method for preparing a therapeutic or diagnostic complex comprised of a nucleic acid ligand and a lipophilic compound or a non-immunogenic, high molecular weight compound. The full text of the above described patent applications, including but not limited to, all definitions and descriptions of the SELEX process, are specifically incorporated by reference herein in their entirety.

Without question, the SELEX process is very powerful. The nucleic acid ligands obtained by the SELEX process have the ability to act in many capacities. One of the capacities that nucleic acids ligands possess is the ability to bind specifically to a target.

The study of biomolecular interactions is of basic importance in understanding processes of molecular recognition and biological function. An area of recent development in understanding biological processes at the molecular level is the use of biosensors to monitor interactions in real time (Jonsson, U. et al., (1992) Advances in Biosensors 2, 291–336). A biosensor may be defined as an instrument that combines a biological recognition mechanism with a sensing device or transducer (Higgins, I. J., Presentation at Biosensors 1989, St. John's College, Cambridge, UK). A range of potentially useful biosensor technologies for real-time interaction studies has been described in the literature (Badley, R. A. et al., (1987) Phil. Trans. R. Soc. Lond. B. 316, 143; Guilbault, G. G. (1988) Analytical Chemistry 19, 1; Heineman, W. R. et al., (1987), Meth. Biochem. Anal. 32, 345; Kretschmann, E. Z., (1971), Physik 241, 313; Kronick, M. N. et al., (1974), Proc. Natl. Acad. Sci., USA 71, 4553; Liedberg, B. et al. (1983) Sensors and Actuators 4, 299; Mosbach, K. and Danielsson, B. (1974) Biochim. Biophys. Acta Report 364, 140; Nellen, P. M. et al., (1990) Sensors and Actuators 1, 592; Roederer, J. E. et al., (1983) Anal. Chem. 55, 2333; Rothern A. (1945) Rev. Sci. Instum. 16, 26; Trunit, Arch. Biochem. Biophys. (1953) 47, 251; Vroman, L. et al., (1969) Surface Sci. 16, 438).

Real-time molecular interaction analysis (Jonsson, U. (1992) Biosensors: Fundamentals, Technologies and Applications. ed. Scheller F. and Schmid R. D., pp 467–476 (GBF Monographs Volume 17)) uses the optical phenomenon of surface plasmon resonance (SPR) technology (Kretschmann, E. and Raether H. (1968) Z. Naturforschung, Teil. A 23, 2135). SPR is a method for monitoring interactions, in real time and without the use of labels, between two or more molecules such as proteins, peptides, nucleic acids, carbohydrates, lipids and low molecular weight molecules such as signaling substances and pharmaceuticals.

Surface plasmon resonance is an optical phenomenon which arises in thin metal films under conditions of total internal reflection. This phenomenon produces a sharp dip in the intensity of reflected light at a specific angle, termed the resonance angle. The position of this resonance angle depends on several factors including the refractive index of the medium close to the non-illuminated side of the metal film. Refractive index is directly correlated to the concentration of dissolved material in the medium. SPR is used in bimolecular interaction analysis to measure changes in the concentration of molecules in a surface layer of solution in contact with the sensor surface.

Real-time molecular interaction analysis uses SPR technology to monitor interactions in real time. The BIAcore 2000 (BIAcore, Inc.) is one type of system available which performs such an analysis. To perform a real-time biomolecular interaction analysis, a target is immobilized on a sensor chip, which forms one wall of a micro-flow cell. A solution containing an analyte that interacts with the immobilized target is then injected over the sensor chip in a controlled flow, during which a monochromatic light is focused on the sensor chip. As analytes from the solution bind to the immobilized target, the surface concentration changes and thus the resonance angle changes and a SPR response is registered. This response is detected as a signal, expressed in resonance units (RU), and is directly proportional to the mass of analytes bound to the target on the sensor chip. The continuous display of RU as a function of time, referred to as a sensorgram, thus provides a complete record of the progress of association and dissociation. When analysis of one interaction cycle is complete, the surface of the sensor chip can be regenerated by treatment with conditions that remove all bound analyte preferably without affecting the activity of the immobilized ligand. Curve fitting analysis of the data in the sensorgrams allows kinetic constants of the interactions to be determined.

The essential components of a SPR biosensor system are: 1) a sensor chip covered with a surface matrix to which targets may be immobilized where the interaction takes place; 2) an optical system responsible for generation and detection of the SPR signal; and 3) a liquid handling system with precision pumps and an integrated micro-fluidic cartridge for controlled transport of samples to the sensor surface.

The sensor chip is a glass slide coated on one side with a thin gold film, to which a surface matrix is covalently attached. This matrix is the means by which biomolecules can be immobilized on the sensor chip surface. One type of sensor chip comprises a matrix which consists of carboxymethylated dextran. A number of chemical techniques can be used to immobilize a target to this matrix, depending on the nature of the interactant and the purpose of the immobilization. Another type of sensor chip has a hydrophobic layer for immobilizing lipophilic substances, such as liposomes, which contain a target in the lipid bilayer of the liposome. The sensor chip may be regenerated for repeated use by exposing the sensor chip to conditions which dissociate and elute the target from the sensor chip, depending on the stability of the immobilized ligand and the severity of the conditions required to elute the analytes.

The use of SPR technology in partitioning high affinity nucleic acid ligands from low affinity nucleic acid ligands in the SELEX process has not been demonstrated so far. The present invention demonstrates that SPR technology can replace the conventional partitioning methods in the SELEX process to obtain high affinity nucleic acid ligands in significantly fewer rounds of SELEX as compared to conventional partitioning methods. The method of the present invention also eliminates the need to radiolabel or tag the nucleic acids as a means of detection, provides a means to perform the SELEX process with much smaller amounts of target than in conventional SELEX methods, and allows for the selection of nucleic acids ligands to a target based on specific kinetic properties in real time.

BRIEF SUMMARY OF THE INVENTION

The method of the present invention, termed Flow Cell SELEX, presents an improved method for partitioning and/or monitoring the partitioning of nucleic acid ligands from a candidate mixture. More specifically, Flow Cell SELEX can partition between high and low affinity nucleic acids ligands to a target. The selection of a desired nucleic acid ligand or a nucleic acid ligand solution to a target is achieved with as few as one or only a few rounds of SELEX and without the use of radiolabels. Specifically, the method of the present invention describes the use of SPR technology in the SELEX process as a partitioning method to obtain high affinity nucleic acid ligands to a target in fewer rounds of SELEX than when conventional partitioning methods are used in the SELEX process.

The Flow Cell SELEX method achieves remarkable partitioning between high and low affinity nucleic acid ligands by immobilizing the desired target on a sensor chip and contacting the immobilized target with a candidate mixture of random nucleic acids, wherein the candidate mixture of nucleic acids is flowed over the surface of the sensor chip. The flow rate can be manipulated to provide for the identification of nucleic acid ligands with specific kinetic properties. In one preferred embodiment, the candidate mixture flows rapidly and only those nucleic acids with a very fast on-rate and slow off-rate or which rebind quickly form nucleic acid/target pairs which accumulate on the sensor chip. The unbound nucleic acids are washed from the flow cell, after which the bound nucleic acids can be eluted from the sensor chip, thereby allowing for the identification of high affinity nucleic acid ligands to the target.

In one embodiment of the invention, the selection process may be efficient enough to provide a ligand solution after only one separation step.

In another embodiment of the Flow Cell SELEX process, the process is iteratively performed until a single or a discrete small number of nucleic acid ligands remain in the candidate mixture following amplification.

In an alternate embodiment of the invention, SELEX iterations are terminated at some point when the candidate mixture has been enriched in higher affinity nucleic acid ligands, but still contains a relatively large number of distinct sequences. This point can be determined by one of skill in the art by periodically analyzing the sequence randomness of the bulk candidate mixture, or by assaying bulk affinity to the target during the SELEX process.

In another embodiment of the invention, the candidate mixture is recycled and flowed over the surface of the sensor chip several times. This results in increased opportunity for rare high affinity molecules to bind to the target and for the bound nucleic acids to be replaced by higher affinity nucleic acids over an extended period of exposure to the target, thus allowing for selection of those nucleic acids with the highest affinity to the target.

The Flow Cell SELEX method is an improvement over prior art partitioning methods. With the method of the present invention, the efficiency of partitioning is increased, and the procedure may be readily automated. In addition, the method of the present invention allows for the selection of nucleic acid ligands to a target based on specific kinetic properties in real time.

Another advantage of the method of the present invention is that the SPR technology detects changes in mass on the sensor chip rather than radioactive emission. Thus, the entire SELEX process can be performed without the use of radioactive labels or other tags as a means of detecting the nucleic acid ligands.

This invention includes a method for identifying a nucleic acid ligand to a target from a candidate mixture of nucleic acids comprising a) immobilizing a target molecule on a sensor chip, b) preparing a candidate mixture of nucleic acids, c) passing the candidate mixture of nucleic acids over the surface of the sensor chip under controlled flow conditions, d) washing the sensor chip to remove unbound nucleic acids, e) eluting the bound nucleic acids optionally amplifying, and f) identifying the nucleic acids which bound to the target, whereby a nucleic acid ligand to a target is identified.

In one embodiment, the stringency of the association conditions is manipulated to select for nucleic acids having specific characteristics. In another embodiment, the stringency of the dissociation conditions is manipulated. In a third embodiment, the stringency of the elution conditions is manipulated.

DETAILED DESCRIPTION OF THE INVENTION

This application presents a method for improved partitioning of nucleic acid ligands identified through the SELEX method. The SELEX method is described in detail in U.S. patent application Ser. No. 07/714,131 filed Jun. 10, 1991 entitled "Nucleic Acid Ligands", now U.S. Pat. No. 5,475,096 and U.S. patent application Ser. No. 07/536,428, filed Jun. 11, 1990 entitled "Systematic Evolution of Ligands by EXponential Enrichment", now abandoned. The full text of these applications, including but not limited to, all definitions and descriptions of the SELEX process, are specifically incorporated herein by reference.

For purposes of clarity and a complete understanding of the invention, the following terms are defined.

"Nucleic Acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the nucleic acid ligand bases or the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, methylations, unusual base-pairing combinations such as the isobases isocytidine and isoguanidine and the like. Modifications can also include 3' and 5' modifications such as capping.

"Nucleic Acid Ligand" as used herein is a non-naturally occurring nucleic acid having a desirable action on a target which comprises two or more nucleotides. A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. In the preferred embodiment, the action is specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. In the preferred embodiment, the nucleic acid ligands are identified through the method known as Flow Cell SELEX. Nucleic acid ligands include nucleic acids that are identified from a candidate mixture of nucleic acids, said nucleic acid ligand being a ligand of a given target by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids.

"Candidate Mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences to facilitate the amplification process surrounding a randomized region of sequences.

"Target molecule" means any compound of interest for which a ligand is desired. A target molecule can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc., without limitation.

"Partitioning" means any process whereby ligands bound to target molecules can be separated from nucleic acids not bound to target molecules. More broadly stated, partitioning allows for the separation of all the nucleic acids in a candidate mixture into at least two pools based on their relative affinity to the target molecule. Partitioning can be accomplished by various methods known in the art. Nucleic acid-protein pairs can be bound to nitrocellulose filters while unbound nucleic acids are not. Columns which specifically retain nucleic acid-target complexes can be used for partitioning. For example, oligonucleotides able to associate with a target molecule bound on a column allow use of column chromatography for separating and isolating the highest affinity nucleic acid ligands. Surface plasmon resonance technology can be used to partition nucleic acids in a mixture by immobilizing a target on a sensor chip and flowing the mixture over the chip, wherein those nucleic acids having affinity for the target can be bound to the target, and the remaining nucleic acids can be washed away. Liquid—liquid partitioning can be used as well as filtration gel retardation, and density gradient centrifugation.

"Ligand Solutions" are defined as the three dimensional structure held in common or as a family that define the conserved components identified through SELEX. Ligand solutions are meant to represent a potentially large collection of appropriate sequence/structures, each identified by the family description which is inclusive of all exact sequence/structure solutions. Although the ligand solution derived by SELEX may include a relatively large number of potential members, the ligand solutions are target specific and, for the most part, each member of the ligand solution family can be used as a nucleic acid ligand to the target.

"Flow Cell SELEX" is a method for identifying a nucleic acid ligand to a target from a candidate mixture of nucleic acids utilizing SPR as the monitoring method in the SELEX process, comprising the steps of a) immobilizing a target molecule on a sensor chip, b) preparing a candidate mixture of nucleic acids, c) passing the candidate mixture of nucleic acids over the surface of the sensor chip in a controlled flow conditions, d) washing the sensor chip to remove unbound nucleic acids, e) eluting the bound nucleic acids and optionally amplifying, and f) identifying the nucleic acids which bound to the target, whereby a nucleic acid ligand to a target is identified.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences.

The fixed sequence regions are selected either: a) to assist in the amplification steps described below; b) to mimic a sequence known to bind to the target; or c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) the candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a certain amount of the nucleic acids in the candidate mixture (approximately 0.1–10%) are retained during partitioning.

4) Those nucleic acids selected during partitioning as having relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for the preparation of the initial candidate mixture; methods for partitioning nucleic acids within a candidate mixture; and methods for amplifying partitioned nucleic acids to generate enriched candidate mixtures. The SELEX Patent Applications also describe ligand solutions obtained to a number of target species, including protein targets wherein the protein is or is not a nucleic acid binding protein.

The method of the present invention presents an improved method for partitioning in the SELEX process between high and low affinity nucleic acid ligands for a target. The method of the present invention has several advantages over prior art methods of partitioning.

Figure 1:
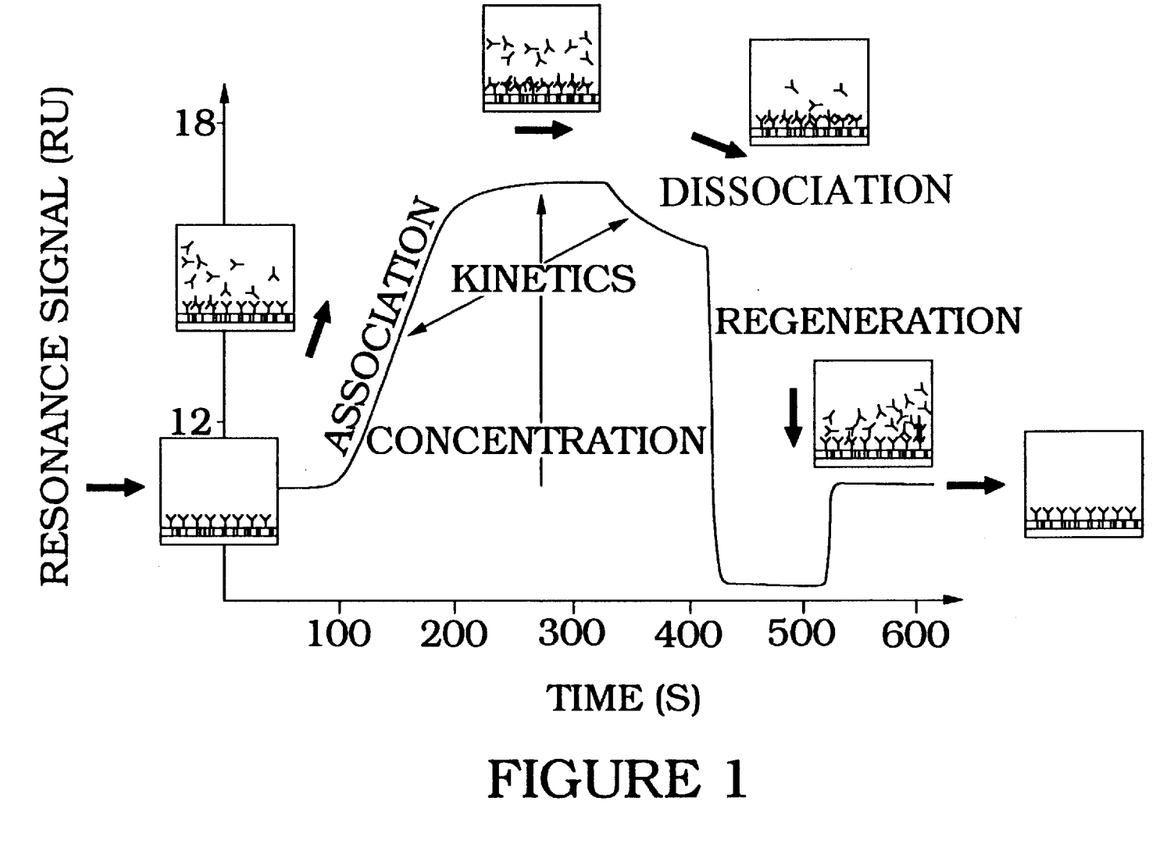
FIG. 1 illustrates the progress of an interaction between a bound ligand and an analyte using SPR technology which is monitored as a sensorgram.

A novel feature of the Flow Cell SELEX method is the means by which the high and low affinity nucleic acids in the candidate mixture are partitioned. The progress of the interaction between the target and the nucleic acids is monitored as a sensorgram (FIG. 1). A sensorgram is a plot of changes in resonance signal as a function of time, expressed in resonance units (RU). The sensorgram is displayed on a computer screen in real time as the experiment progresses. The progress of an interaction is followed by observing the change in resonance signal. In Flow Cell SELEX the target is immobilized on a sensor chip and a candidate mixture of nucleic acids is passed over the sensor chip under controlled flow. Nucleic acids bind to the immobilized target during the sample injection, resulting in an increase in signal. The signal can be reported on a sensorgram and the steepness of the curve reflects the association rate constant (ka) of the interaction of the nucleic acids with the target. The plateau of the curve is a direct measure of the total accumulated mass of nucleic acids and is dependent on the concentration of binding nucleic acids in the applied candidate mixture. At the end of the application, the sample is replaced by a continuous flow of buffer and the shape of the curve in the sensorgram is a measure of the decrease in signal and reflects the dissociation rate constant (kd) of the bound nucleic acids. The remaining bound nucleic acids are removed from the sensor chip by regeneration or elution with an appropriate buffer which disrupts the binding interaction of the bound nucleic acids with the immobilized target. After elution, the sensor chip is washed with the continuous flow buffer to return the signal to baseline. The ka and kd are then determined from the sensorgram data using a non-linear curve fitting algorithm.

In the candidate mixture, there exists only a very small number of nucleic acids with high affinity for the target that can bind to the target molecule. Flow Cell SELEX typically uses very rapid flow conditions. For example, an entire column volume can be flowed over the sensor chip every second. Therefore only those nucleic acids with very high ka values bind to the target. The selection for nucleic acids with high ka values in Flow Cell SELEX can be achieved by manipulation of the association conditions, such as flow rate or buffer composition.

Early in the SELEX process association plateau levels are low. This reflects the extremely low concentration of high affinity nucleic acids present in the candidate mixture which are able to bind to the immobilized target. As SELEX progresses, the association plateau level increases, reflecting the increase in concentration of high affinity nucleic acids in the candidate mixture. The steepness of the association curve also increases as SELEX progresses. This reflects the increase in the concentration of nucleic acids with higher ka values in the candidate mixture.

During the dissociation phase, the decrease in the resonance signal reflects the rate at which the bound nucleic acids dissociate from the immobilized target. As dissociation time increases, those nucleic acids with higher kd values will dissociate and be removed, and those with lower kd values will remain bound to the immobilized target. This results in an enrichment for nucleic acids with low kd values. Therefore, the dissociation time can be adjusted to facilitate this enrichment. By observing the sensorgram, the time at which the bound nucleic acids are to be eluted can be determined.

Thus, for the first time, the present invention allows for the selection of high affinity nucleic acid ligands to a target, in real time, based on a desired kinetic property. For example, Flow Cell SELEX offers a significant advantage for selecting for an effective nucleic acid ligand, that is, one which has a very fast association rate with the target of interest and a slow off rate. Various parameters of Flow Cell SELEX can be manipulated to identify nucleic acid ligands with any kinetic property.

In the SELEX method, described by Tuerk and Gold in U.S. Pat. No. 5,475,096, which is incorporated herein by reference, a nucleic acid candidate mixture is generated and contacted with a target molecule. Nucleic acid sequences with enhanced affinity to the target molecule form nucleic acid-target complexes. This is followed by partitioning of bound and unbound nucleic acids, and separation of the target molecule from the bound nucleic acids. The cycle is repeated until the complexity of the candidate mixture has decreased and its affinity as well as specificity to the target has been maximized.

Prior art partitioning methods included use of nitrocellulose filter binding or an affinity column. Unlike an equilibrium system, where the affinity of a heterogeneous library is influenced heavily by the excess of low affinity species, the flow system in Flow Cell SELEX typically only detects the high affinity species and measures the affinity of this subset of the library. For this reason, kd values, and therefore Kd values of the early rounds of Flow Cell SELEX will be lower than the corresponding rounds of SELEX which use conventional partitioning methods. Flow Cell SELEX parameters can optionally be selected for equilibrium conditions if desired.

One disadvantage of the prior art partitioning was the phenomenon of matrix binders in which nucleic acids that specifically bind the partitioning matrix as well as nucleic acids which are physically trapped in the matrix are selected along with those that specifically bind the target. One advantage of the method of the present invention is that it appears to overcome unwanted selective pressure originating with use of a partitioning matrix by using flow conditions wherein only those nucleic acids which have a very high affinity for the target remain bound to the target.

The method of the present invention offers an advantage over previous methods of partitioning in that it allows for higher enrichment for the high affinity nucleic acids in each cycle of SELEX leading to a faster identification of the desired nucleic acid ligand or ligand solution. In traditional partitioning methods, it is desirable to set the partitioning criteria so that a significant amount of the nucleic acids in the candidate mixture (approximately 0.1–10%) are retained during partitioning and are used in the next cycle of SELEX. This value (signal) must be high in order to exceed the moderate level of target-independent retention and non-specific target-dependent retention (noise) that accompanies traditional partitioning methods, generally 0.1–10%. The method of the present invention shows little or no detectable noise, allowing the partitioning criteria to be set such that a much smaller amount of nucleic acids in the candidate mixture are retained during partitioning (0.001–0.01%).

For example, in partitioning methods which rely on radioemission for detection, the signal/noise reflects a certain amount of non-specific signal, and therefore it is necessary to retain a larger percentage of the candidate mixture for the next round of SELEX. In the method of the present invention, only a smaller amount, for example, femtamolar amount, more particularly, 100 femtamoles of the candidate mixture can bind to the sensor chip. To date, the maximum concentration of target immobilized on the sensor chip was 100–150 femtamoles, however, concentration can be optimized both up and down. Assuming 100 fm immobilized target, a candidate mixture of nucleic acids containing 1 nmole (i.e., 1,000,000 femtamoles) flowing over the sensor chip, the maximum amount of the candidate mixture that could bind to the target is approximately 100 fmoles/1,000,000 fmoles, or 0.01%. Thus, it is necessary that the signal/noise partitioning be excellent. As such, only the specific binding nucleic acids will be detected, and the partitioning for the higher affinity binding nucleic acids each round will be greatly enhanced.

The method of the present invention provides the ability to monitor association, dissociation, and elution kinetics of the nucleic acids in real time and under flow conditions relevant to physiologic shear in post-capillary venules. For example, if specific kinetic properties are required for a blood pool nucleic acid ligand to interact with and tightly bind its target, the method of the present invention offers a unique opportunity for discovering these ligands. That is, using SPR technology as the partitioning method, it is possible to observe in real time the kinetic properties of the candidate mixture of nucleic acids. Therefore, one can program the instrument to elute those nucleic acids having the observed desired binding properties rather than performing a separate kinetic study of the nucleic acid ligands after the SELEX process is complete.

Another advantage of the method of the present invention is that the method of detection in the partitioning step used in the Flow Cell SELEX depends on a change in mass rather than radioemission. Therefore the method of the present invention can be performed without the use of radiolabels or any kind of tag to detect the high affinity nucleic acids.

The present invention provides a method for identifying nucleic acid ligands to a target from a candidate mixture of nucleic acids comprising a) immobilizing a target on a sensor chip, b) preparing a candidate mixture of nucleic acids, c) injecting the candidate mixture of nucleic acids over the surface of the sensor chip in a controlled flow, d) washing the sensor chip to remove unbound nucleic acids, e) eluting the bound nucleic acids and optionally amplifying and f) identifying the nucleic acid ligands which bound to the target. A significant advantage of the present invention is that it allows for more effective partitioning of high affinity nucleic acids from low affinity nucleic acids, wherein the number of cycles of the SELEX process needed to be performed until the affinity of the nucleic acids to the target is maximized is much less than with traditional partitioning methods. Therefore, one feature of the invention is its ability to partition strong and weak affinity nucleic acids rapidly.

The method of the present invention offers an advantage over soluble target SELEX in that the solubility properties of the target are not an issue in determining whether the SELEX method can be used to find a nucleic acid ligand to a target. This is because the target is immobilized on the sensor chip rather than solubilized in the SELEX buffer solution. One type of sensor chip available comprises a carboxymethylated dextran matrix. A wide range of chemical techniques known in the art can be used to immobilize the target to the dextran matrix, depending on the chemical nature of the target. For example, the target can be directly coupled the matrix through methods such as amine coupling, thiol coupling, or aldehyde coupling. Another type of sensor chip available is one where the matrix has been modified with streptavidin for direct immobilization of biotinylated targets. Furthermore, sensor chips are available which have a hydrophobic surface, and these can be used to immobilize lipophilic substances, such as liposomes, which include a ligand contained in the lipid bilayer of the liposome. Thus, the method of the present invention allows for the identification of nucleic acid ligands to targets which were previously very difficult to use under conditions used in the conventional SELEX method due to difficulties in solubilizing the target in the SELEX solutions.

The target can be a protein (either nucleic acid or non-nucleic acid binding protein), peptide, carbohydrate, polysaccharide, glycoprotein, hormone, receptor, antigen, antibody, virus, substrate, metabolite, transition-state analog, cofactor, inhibitor, drug, dye, nutrient, growth factor, or liposome, as long as it is possible to immobilize the target on the sensor chip.

The candidate mixture of nucleic acids includes any nucleic acid or nucleic acid derivative, from which a complementary strand can be synthesized. The individual test nucleic acids can contain a randomized region flanked by conserved regions in all nucleic acids in the mixture. The conserved regions are provided to facilitate amplification of selected nucleic acids. Since there are many such sequences known in the art, the choice of sequence is one which those of ordinary skill in the art can make, having in mind the desired method of amplification.

In one embodiment of the present invention, the candidate mixture is flowed over the surface of the sensor chip on which the target is immobilized in one or more aliquots. The sensor chip is washed with a buffer to remove any non-specifically bound or low affinity nucleic acids. This is followed by elution of the high affinity nucleic acids, which are then recovered, pooled, precipitated, reverse transcribed, amplified by PCR and gel purified. This higher affinity pool of nucleic acids is then used in the next cycle of Flow Cell SELEX, and the cycles are repeated until the desired conditions are obtained, such as the sensorgram reflects saturable association.

In another embodiment of the invention, the candidate mixture is flowed over the sensor chip, buffer is used to remove the non-specifically bound or low affinity nucleic acids, and the unbound RNAs in the candidate mixture are collected and recycled over the sensor chip several times to increase the probability that each unique nucleic acid interacts with the target. After several cycles have been performed, the sensor chip is washed with a buffer, and then the high affinity nucleic acids are eluted. In a preferred embodiment, the candidate mixture is recycled four times.

In a preferred embodiment of the invention, the candidate mixture is flowed over the surface of the sensor chip in several aliquots, the low affinity nucleic acids are removed to waste with a buffer, and the high affinity nucleic acids are eluted prior to the next injection of an aliquot of the candidate mixture. The association time that would be required to flow the entire candidate mixture over the sensor chip in one application would necessarily be much longer than if the candidate mixture was applied in smaller aliquots. This would place a higher stringency on those nucleic acids that bind to the immobilized target immediately after the candidate mixture is passed over the sensor chip to remain bound during the entire time it takes for the entire candidate mixture to pass over the sensor chip. This stringency is decreased if the candidate mixture is passed over the sensor chip in several smaller aliquots.

The experimental conditions used in the selection of nucleic acid ligands using the Flow Cell SELEX method can be manipulated to optimize the selection of nucleic acid ligands having specific predetermined properties and to mimic the environment that the target would be found in vivo. Adjustable conditions that may be altered to select for certain kinetic properties or more accurately reflect the in vivo environment of the target include, but are not limited to, the target density on the sensor chip, the nucleic acid concentration, buffer components (e.g., total ionic strength, the concentration of bivalent cations, the pH of the solution, the addition of urea or detergent), flow rate, association time, dissociation time, the addition of a soluble target (competitor) to prevent rebinding, eluent components, elution time.

In a further embodiment of the invention, the Flow Cell SELEX method is automated.

The method of the present invention allows for the identification of a nucleic acid ligand or a nucleic acid ligand solution to a target in fewer rounds that in the conventional SELEX process. In Example 2, a Flow Cell SELEX process is described in which a high affinity nucleic acid ligand solution to human L-Selectin chimera is obtained after 5 rounds of Flow Cell SELEX. This is compared to the method reported in WO96/40703, which is incorporated herein by reference, in which a high affinity nucleic acid ligand to human L-Selectin chimera(LF1613) (SEQ ID NO: 6) was obtained after 12 rounds of conventional SELEX to L-Selectin chimera immobilized on beads. It was observed that the $K_d$ of the nucleic acid ligand solution pool obtained after round 5 from Flow Cell SELEX was comparable to the $K_d$ of an isolated high affinity nucleic acid ligand obtained after 12 round of traditional SELEX.

Example 3 describes a Flow Cell SELEX in which the dissociation flow rate is adjusted or soluble target protein is included in the dissociation buffer. The nucleic acids bound to the immobilized target which have fast off-rates will bind to the soluble target in the dissociation buffer. This method allows for the selection of nucleic acid ligands with a slower off-rate.

The following non-limiting examples illustrate the method of the present invention.

EXAMPLE 1

Materials and Methods
Preparation of the Candidate RNA Mixture.

A candidate mixture of 2'F RNA molecules was made according to previously reported methods (WO96/40703). The following DNA oligonucleotides were synthesized by Operon Technologies and purified to size homogeneity by polyacrylamide gel electrophoresis (PAGE) on a 20% acrylamide, 7M urea denaturing gel:

$30N7_{BIA}$ -
5'-TCGGGCGGAATTCAGG-[N]$_{30}$-CCGCATCGTCCTCCC-3'
(SEQ ID NO: 1)

$5P7_{BIA}$
5'-TAATACGACTCACTATAGGGAGGACGATGCGG-3'
(SEQ ID NO: 2)

$3P7_{BIA}$
5'-TCGGGCGGAATTCAGG-3'
(SEQ ID NO: 3)

Three nanomoles of $5P7_{BIA}$ were incubated with two nanomole of $30N7_{BIA}$- in a 60 µl reaction containing 25 mM Tris-HCl, pH 7.5, 30 mM NaCl, 12 mM MgCl$_2$, and 6.7 mM DTT for 5 minutes at 95° C. and cooled to room temperature to allow the complementary regions of the DNA to anneal. The 3' ends were extended by adding the annealed DNA mixture to a 100 µl reaction containing 25 mM Tris-HCl, pH 7.5, 30 mM NaCl, 12 mM MgCl$_2$, 6.7 mM DTT, 1 mM dNTPs, and 13 units Sequenase DNA polymerase (United States Biochemical), and incubating for 60 minutes at 37° C. The double-stranded extension product was purified to size homogeneity (78 nucleotides) by PAGE on an 8% non-denaturing acrylamide gel. In vitro transcription of the double-stranded DNA was performed in a 1 ml reaction containing 200 nM DNA substrate, 1 mM each of GTP and ATP, 3 mM each of 2'F UTP and 2'F CTP (United States Biochemical), and 200 nM T7 RNA Polymerase in 40 mM Tris-HCl, pH 8.0, 12 mM MgCl$_2$, 5 mM DTT, 1 mM spermidine, 0.002% Triton X-100, and 4% PEG-8000. The reaction was incubated for 16 hours at 37° C. and stopped by addition of 20 units of RQ1 RNase-free DNase (Promega) and further incubation for 10 minutes at 37° C. The RNA was purified to size homogeneity (61 nucleotides) by PAGE on an 8% acrylamide, 7M urea denaturing gel. This 2'F pyrimidine, 2'OH purine RNA comprised the candidate mixture for the SELEX.

L-Selectin-Ig Fusion Protein

A. Plasmid construction

A vector for the stable mammalian cell expression of human L-selectin receptor globulin (LsRg) consisting of the extracellular domain of human L-selectin fused to the amino-terminus of the hinge and CH1 and CH2 domains of the human IgG1 heavy chain was constructed as follows: The Fc coding portion within the pIG vector was excised by digestion with BamHI and XbaI. This fragment was cloned into the corresponding BamHI and XbaI sites within the mammalian expression plasmid pCDNA3.1 (Invitrogen, San Diego, Calif.). This latter vector contains the neomycin resistance gene. A DNA fragment coding for the leader sequence and extracellular domain of L-selectin was obtained by a PCR strategy using the L-selectin cDNA clone as template. The 5'-primer, 5'-GACCAAGCTTAGCCATGATATTTCCATGGAAA-3' (SEQ ID NO: 4); contained a HindIII site (underlined) while the 3'-primer; 5'-GCCAGGATCCACTTACCTGTGTTATAATCACCC TCCTTAATC-3' (SEQ ID NO: 5), contained a BamHI site (underlined) followed by a splice donor site (bold text). Following PCR, 1.0 kb fragment was restricted with BamHI and HindIII and inserted into the corresponding sites within the modified pCDNA.3.1 vector, downstream of the CMV promoter, to create pCDNA-LS-Rg. The sequence of LS-Rg was confirmed by standard DNA-sequencing methods.

B. Cell culture

Stable expressing LS-Rg CHO cell lines were produced by transfection of pCDNA-LS-Rg by the $CaCl_2$ precipitation method. The day after transfection, the cells were fed with Ham's F12 media containing 10% FBS. 36 hours after transfection the cells were fed as before except the media contained 300 mg/ml geneticin (G418-sulfate; Gibco-BRL, Gaithersberg, Md.). Selection was allowed to proceed until individual colonies could be isolated. Isolated colonies were expanded under selection conditions and analyzed for LS-Rg production.

For LS-Rg production, A CHO clonal cell line was expanded until approximately 80% confluence. At that time the cells were either transferred into Ham's F12 media containing no serum or 10% FBS. Four days later the media was harvested and clarified by centrifugation at 2,830×g for 20 minutes. Clarified supernatant was used for column chromatography.

C. Affinity Chromatography

Protein-A chromatography was performed using 1 ml Hightrap columns. (Pharmacia). All column procedures were carried out at 4° C. Conditioned media was loaded at 2 ml/min and, after loading was completed, the column was washed with 20 column volumes of Dulbecco's PBS. Elution was performed using 0.1M sodium citrate pH 3.0. Eluted fractions were immediately neutralized with 1M Tris-HCl pH 8.0. Neutralized fractions could be loaded directly onto the AAC column.

The AAC column was prepared by incubation, in PBS, of 1.6 mg of the biotinylated L-selectin DNA-aptamer with 1 ml of Ultralink immobilized streptavidin Plus (Pierce, Rockford, Ill.). The incubation was performed for 2 hours at 4° C. with continuous mixing. Following the incubation the column was extensively washed with PBS. The percentage of oligonucleotide coupled to the resin (1.1 mg) was determined by measuring the UV absorbance, at 260 nm, of the unbound-DNA fraction and subtracting this value from the initial absorbance. Coupled resin was stored at 4° C.

Chromatography was performed at room temperature using an HPLC system consisting of a Waters model 625 gradient pump, a Waters model 600E system controller, and a Waters model 490 multi-wavelength detector. Fractions were collected by hand. The column (0.5×5 cm) was equilibrated and washed with Dulbecco's PBS containing divalent cations.

D. Protein Concentration Determination

Protein concentrations were determined by a modification of the method of Bradford using the Bio-Rad Protein assay kit according to the manufacturer's directions (Bio-Rad Laboratories, Hercules, Calif.).

SPR Biosensor and Preparation of sensor chips

All Flow Cell SELEX experiments were carried out with a BIAcore 2000 biosensor (Biacore, Inc., formerly Pharmacia Biosensor AB, Uppsala). Targets were immobilized on carboxymethylated dextran on research-grade CM-5 sensor chips (Pharmacia) using standard N-ethyl-N'-(dimethylaminopropyl)carbodiimide/N-hydroxysuccinimide coupling. Proteins were diluted in appropriate coupling buffer (human L-selectin Ig fusion protein, 10 mM sodium acetate buffer, pH 5.0) and incubated with activated sensor chips for various times and at various concentrations to optimize the degree of derivatization needed for particular experiments. After coupling, excess N-hydroxysuccinimide groups were inactivated with ethanolamine HCl. Control flow cells were mock-derivatized by activating and then inactivating with ethanolamine without the addition of protein. Chips were regenerated by 1 minute pulses with HEPES buffered saline (HBS) (10 mM HEPES, 150 mM NaCl, 3.4 mM EDTA) with additional 1M NaCl and 10 mM EDTA unless otherwise noted. Control experiments showed that L-selectin chimera-derivatized dextran was able to withstand 24 rounds of regeneration without losing significant binding capacity. All sensor chips were subjected to several rounds of analyte binding and regeneration at several temperatures to ensure a stable level of derivatization. Mobile phase for immobilization was HBS. Mobile phase for the SELEX experiments was SHMCK buffer (111 mM sodium chloride, 5 mM potassium chloride, 1 mM calcium chloride, 1 mM magnesium chloride and 20 mM HEPES, pH 7.5,) containing 0.005% P20 surfactant.

The Biacore kinetic data analyses were performed using BIAevaluation2.1 software (Pharmacia).

Nitrocellulose filter binding assays were carried out as previously described (Tuerk and Gold, (1990) *Science*, 249, 505–510)

Amplification of the Eluted RNA

The eluted RNA was EtOH precipitated with 100 pmoles of 3P7BIA as a nucleic acid carrier and resuspended in 10 μl $dH_2O$. The RNA was reverse transcribed to cDNA in a 20 μl reaction containing an additional 100 pmoles of $3P7_{BIA}$, 1 mM dNTPs, 50 mM Tris-HCl, pH 8.3, 60 mM NaCl, 6 mM $Mg(OAc)_2$, 10 mM DTT, and 20.5 units AMV Reverse Transcriptase (Life Sciences, Inc.), and incubated for 30 minutes at 37° C. The cDNA was then amplified by the polymerase chain reaction (PCR) in a 100 μl reaction containing 500 pmoles each of primers $3P7_{BIA}$ and $5P7_{BIA}$, 1 mM dNTPs, 10 mM Tris-HCl, pH 8.4, 50 mM KCl, 7.5 mM $MgCl_2$, 50 μg/ml BSA, and 5 units AmpliTaq DNA Polymerase (Perkin Elmer). The reaction was prepared on ice, incubated at 93° C. for 3 minutes, and cycled 15 times at 93° C. for 30 seconds, 55° C. for 10 seconds, and 72° C. for 60 seconds in a thermal cycler (MJ Research, Inc., Model PTC-150). 50 μl of the double-stranded PCR product was then transcribed in vitro and purified to size homogeneity as described above. The RNA was resuspended in dH$_2$O and used as the partially-enriched candidate mixture for the next partition step.

EXAMPLE 2

Flow Cell SELEX to human L-Selectin

The Flow Cell SELEX was performed in order to isolate high affinity nucleic acid ligands to human L-Selectin. The materials and methods used in this example are described in Example 1.

To sample a sufficiently large number of different RNA molecules each selection, we applied 1 nmole of the candidate mixture at a concentration of 5 μM in each partition step. To increase the probability that each different RNA molecule would interact with a target molecule in the first round, we minimized the flow rate (3 μl/min) and passed the candidate mixture over the chip multiple times. To increase the probability that each different RNA molecule would interact with a target molecule in rounds 2–5, we decreased the residence time for bound species during the association phase to 20 minutes by applying the candidate mixture in several small aliquots rather than one large aliquot. Following is a detailed description of the partition steps of the SELEX.

Round 1. 1 nmole of the candidate mixture of RNA was diluted in 200 μl SHMCK+0.005% P20. 100 μl was applied to the target on the chip at 37° C. at a flow rate of 3 μl/min (association time=33 min.). The flow-through of unbound RNA was then returned to the original RNA sample, during which time 39 μl SHMCK+P20 was passed over the chip at a flow rate of 3 ul/min (dissociation time=13 minutes). During this recovery step, low affinity RNAs dissociated from the target and were discarded. This process was repeated 3 more times for a total of four applications of 100 μl RNA. Because no recovery was needed after the fourth application, only 1.5 minutes of dissociation elapsed before the elution step. A total of 172.5 minutes elapsed from the time of the first application to the time of elution. To collect the bound RNAs, 60 μl of elution buffer (HBS plus 3.3M NaCl, 10 mM EDTA) was applied at a flow rate of 30 ul/min (elution time=2 minutes). The eluted RNAs were pooled and amplified.

Round 2. 1 nmole of the enriched candidate mixture of RNA was diluted in 200 ul SHMCK+0.005% P20. 60 μl was applied to the target on the chip at 37° C. at a flow rate of 3 ul/min (association time=20 min). The flow-through of unbound RNA was discarded. Buffer flow resumed and the flow rate was increased to 30 μl/min for a dissociation time of 1.5 minutes, during which time low affinity RNAs dissociated from the target and were discarded. To collect the bound RNAs, 60 μl of elution buffer (HBS plus 3.3M NaCl, 10 mM EDTA) was applied at a flow rate of 30 μl /min (total elution time=2 minutes). This process was repeated two more times for a total of three applications of 180 μl RNA. The eluted RNA samples were pooled and amplified.

Round 3. Same as Round 2, except the dissociation time was increased to 11 minutes and the 3.3M NaCl was removed from the elution buffer to select only for divalent cation dependent binders.

Round 4. Same as Round 3, except the dissociation time was increased to 31 minutes.

Round 5. Same as Round 3, except the dissociation time was increased to 60 minutes.

Results

Quantitative results of selections 1–5 are shown in Table 1. Because the amount of bound and subsequently eluted RNA was so low each round, the degree of enrichment was extremely high. Between 0.001% and 0.002% of the sampled RNA was recovered, resulting in a theoretical enrichment for high affinity binders of 10,000-fold in selection round 5 and exceeding 100,000-fold in selection rounds 1 and 2.

TABLE 1

Flowcell SELEX to human L-selectin tg using 30N7BIA 2F Py RNA

| | Association Phase | | | Dissociation Phase | | Elution Phase | | |
|---|---|---|---|---|---|---|---|---|
| Round # | Association Time (min) | Injections and Elutions | RNA Bound | Dissociation time (min) | Percent RNA dissociated before elution | Eluant HBS with: | Eluted RNA | Percent of Total RNA Recovered |
| 1 | 132 | 4 with recycling | ND | 13 | — | NaCl 3.3M EDTA 10 mM | 9 fmoles | 0.0009% |
| 2 | 60 | 3 | ND | 1.5 | — | NaCl 3.3M EDTA 10 mM | 4 fmoles | 0.0004% |
| 3 | 60 | 3 | 63 fmoles | 11 | 58% | EDTA 10 mM | 26 fmoles | 0.0026% |
| 4 | 60 | 3 | 89 fmoles | 31 | 92% | EDTA 10 mM | 7 fmoles | 0.0007% |
| 5 | 60 | 3 | 107 fmoles | 60 | 79% | EDTA 10 mM | 23 fmoles | 0.0023% |

Following Round 5 we measured the affinity of each candidate mixture using the BIAcore 2000 and compared them with the affinity of LF1613, (SEQ ID NO: 6) a high affinity (Kd=100 pM) 2'F Py RNA isolated from a SELEX targeting LsRg immobilized on beads which is described in WO96/40703, which is incorporated herein by reference. These measurements were made using a chip with three flow cells prepared as described in Example 1 but with a lower density of LsRg, and a control mock-derivatized flow cell. The data from the control flow cell were subtracted from the data from the LsRg flow cells before kinetic analysis. Representative sensorgrams for each candidate mixture and LF1613 are illustrated in FIG. 2.

The nested set of curves demonstrate the convergence of the candidate mixtures to a maximum saturation level. During the association phase, only the highest affinity molecules remain bound (low affinity molecules flow to waste).

The dissociation phase then reflects only the kinetic properties of the bound (highest affinity) molecules present in the mixture being assayed. The saturation level of the early rounds is a measure of the fraction of the candidate mixture represented by high affinity molecules. Unlike an equilibrium system, where the affinity of a heterogeneous candidate mixture is influenced heavily by the excess of low affinity species, this flow system only detects the high affinity species and measures the affinity of this subset of the mixture. For this reason, the dissociation rate constant ($k_d$ value), and, therefore, the equilibrium dissociation constant ($K_d$ value) of a partially enriched candidate mixture vary with the method of determining kinetic the constants (see FIG. 3).

Figure 2:
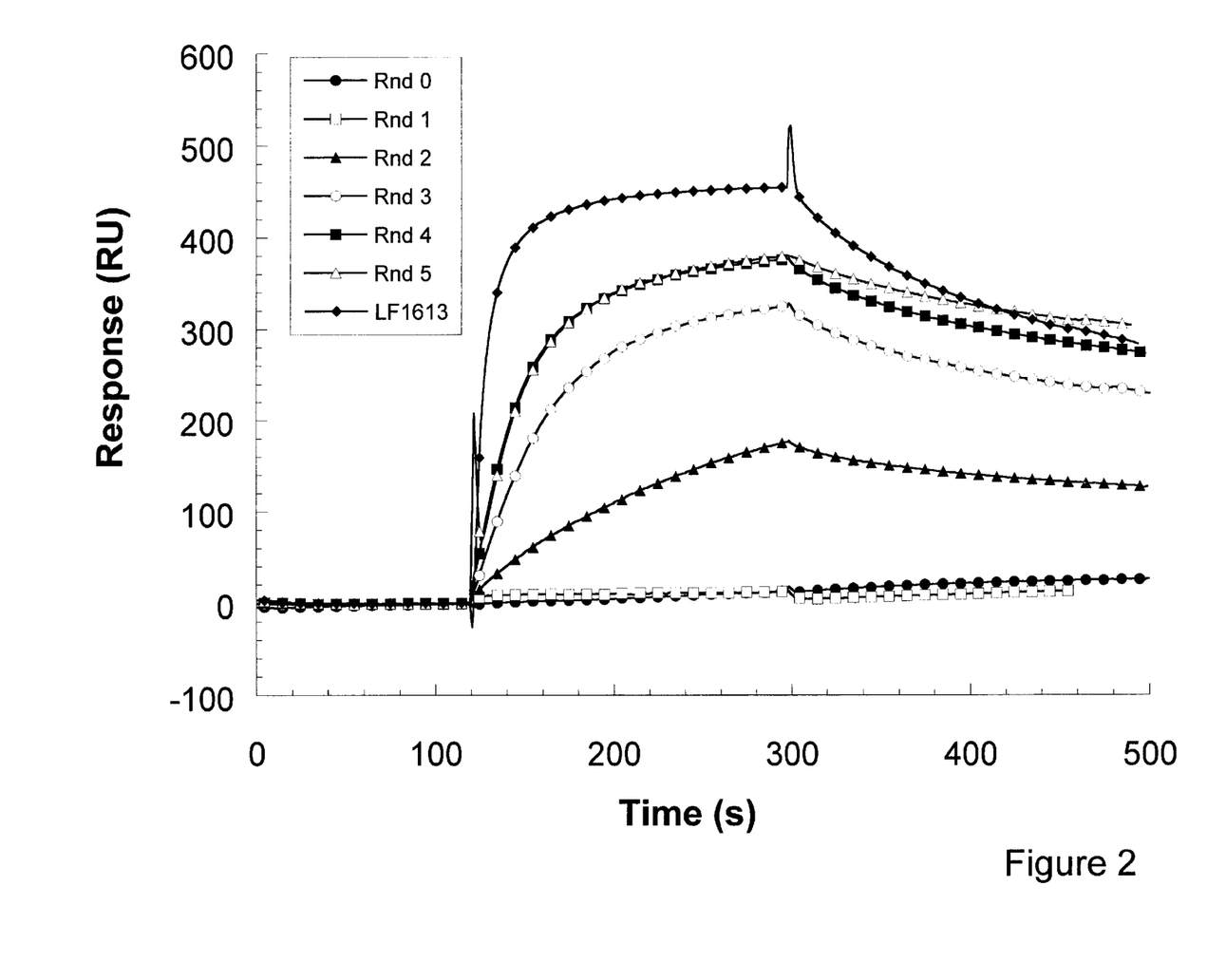
FIG. 2 shows the affinity sensorgrams of random RNA, rounds 1–5 of the Flow Cell SELEX performed on L-Selectin (Example 2) as compared to the affinity sensorgram of LF1613.

Kinetic constants derived from the sensorgrams in FIG. 2 are shown in Table 2. Response levels of the random candidate mixture and the amplified RNA after selection 1 (Rnd 1) were too low to measure accurate kinetic values. The $k_a$ values increase with each round. The selection is for faster on-rates ($k_a$) and, thus, for faster rebinders. On the derivatized flow cell, the target protein is present at a very high density. Dissociated molecules rebind to the target before they flow through the flow cell if they have a fast on-rate. $k_d$ values don't change from Rnd 2 to Rnd 5, maintaining a dissociation $t_{1/2}$ between 6.1 and 7.7 minutes. $K_d$ values drop between Rnd 2 and Rnd 5, leveling off at approximately 4 nM.

TABLE 2

Summary of Kinetic Constants

| RNA | $k_a$ (M$^{-1}$s$^{-1}$) | $k_d$ (s$^{-1}$) | $K_d$ (M) | $t_{1/2}$ (min) |
|---|---|---|---|---|
| Random | — | — | — | — |
| Rnd 1 | — | — | — | — |
| Rnd 2 | $1.7 \times 10^4$ | $1.8 \times 10^{-3}$ | $1.1 \times 10^{-7}$ | 6.4 |
| Rnd 3 | $4.9 \times 10^4$ | $1.9 \times 10^{-3}$ | $3.9 \times 10^{-8}$ | 6.1 |
| Rnd 4 | $7.5 \times 10^4$ | $1.8 \times 10^{-3}$ | $2.4 \times 10^{-8}$ | 6.4 |
| Rnd 5 | $3.7 \times 10^5$ | $1.5 \times 10^{-3}$ | $4.1 \times 10^{-9}$ | 7.7 |
| LF1613 | $1.0 \times 10^5$ | $2.8 \times 10^{-3}$ | $2.8 \times 10^{-8}$ | 4.1 |

The sensorgram saturation levels in FIG. 2 and $K_d$ values in Table II suggested further rounds with this selection scheme would be unnecessary. There is very little change in affinity between Rnd 4 and Rnd 5, both exhibiting a $K_d$ value lower than LF1613. It is expected that individual nucleic acids with affinities equal to or greater than LF1613 exist in the Rnd 5 candidate mixture.

Figure 3:
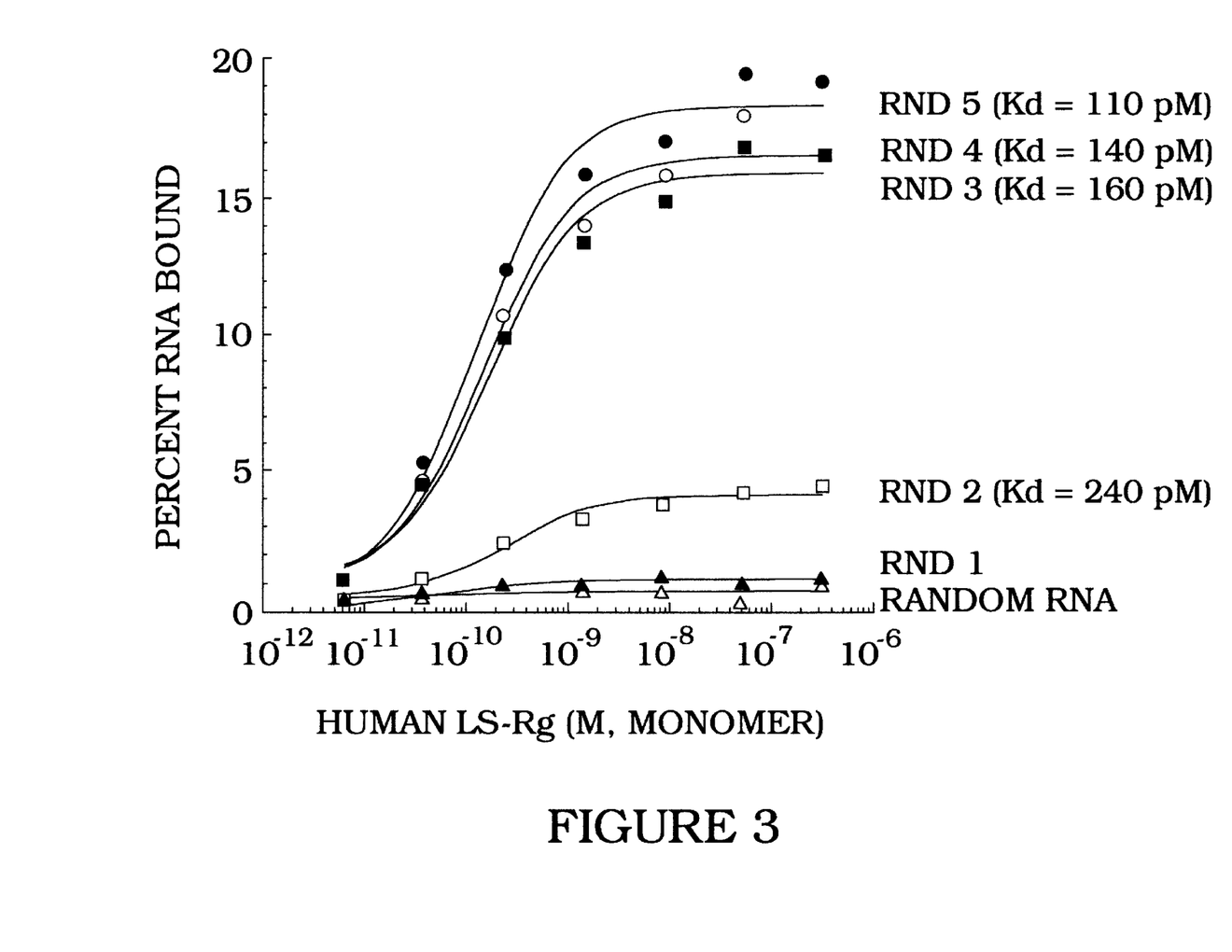
FIG. 3 show the nitrocellulose filter binding curves of random RNA, rounds 1–5 of the Flow Cell SELEX performed on L-Selectin from Example 2.
Figure 4:
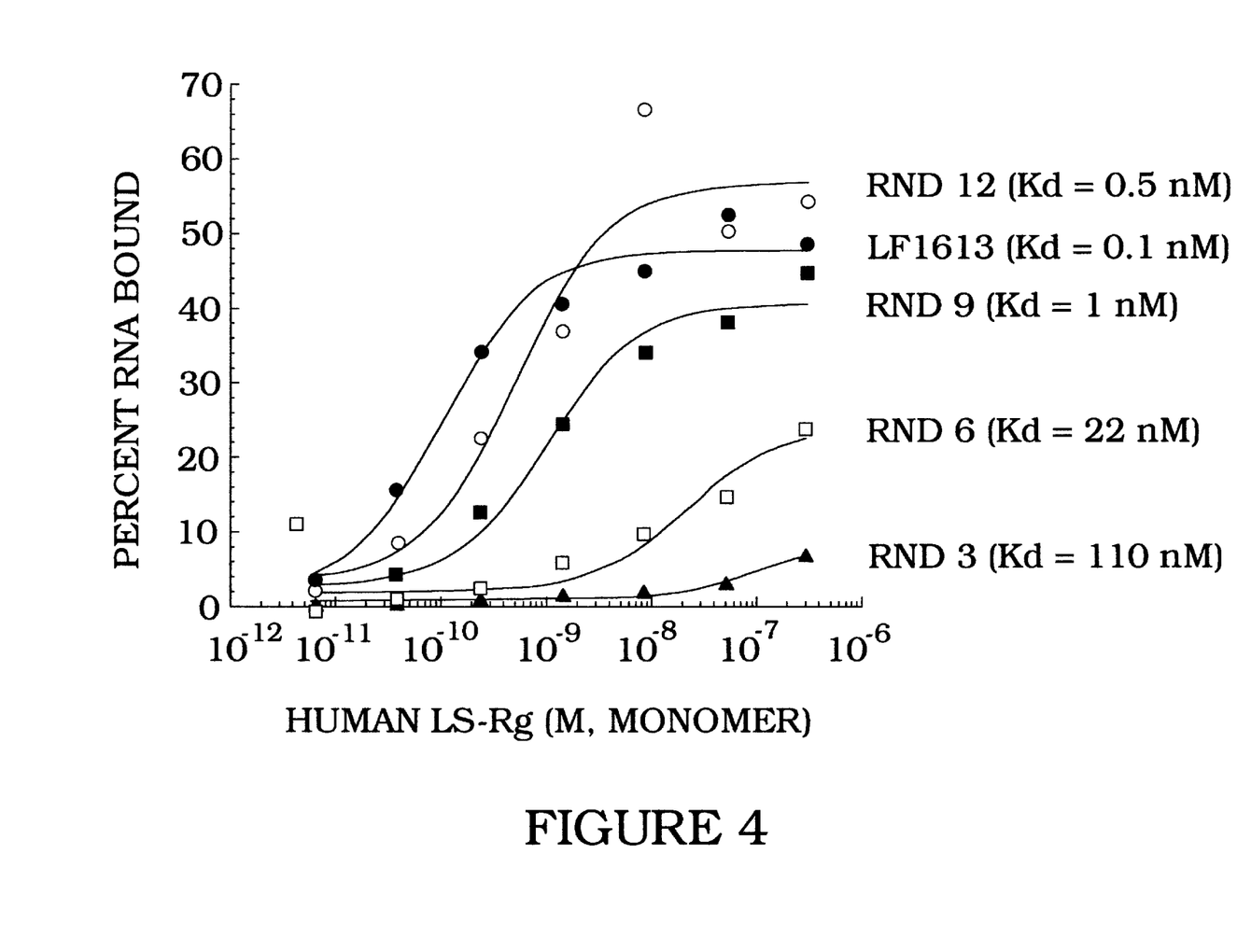
FIG. 4 shows the nitrocellulose filter binding curves of Bead SELEX rounds 3, 6, 9, 12 and LF1613.

An alternative method for measuring affinity of the candidate mixtures is by nitrocellulose filter binding. We measured the affinity of each candidate mixture and LF1613 using the filter binding method. We compared the binding curves of the flow cell SELEX candidate mixtures (FIG. 3) with candidate mixtures from a previous SELEX targeting LsRg immobilized on beads (FIG. 4).

Both SELEXes achieved a candidate mixture affinity less than 1 nM. However, while the candidate mixture affinity of the bead SELEX improved incrementally over the course of the 12 rounds, the candidate mixture affinity of the Flow Cell SELEX very rapidly reached 160 pM (by round three), and only improved slightly with rounds 4 and 5. It is interesting to compare the plateau levels of the final candidate mixtures. The bead SELEX candidate mixture plateaus at approximately 60% bound, while the Flow Cell SELEX candidate mixture plateaus at less than 20% bound. The low plateau suggests that only a portion of the RNA species in the final candidate mixture are high affinity, or that the RNA species in the final candidate mixture exist in multiple conformations, only a fraction of which are in a high affinity conformation at any one time.

EXAMPLE 3

Manipulation of dissociation conditions

The Flow Cell SELEX Round 2 of Example 2 was submitted to several different dissociation conditions to demonstrate that the dissociation conditions can be manipulated to avoid selection of fast rebinders. This manipulation allows direct selective pressure for slow off rates to be applied in the SELEX.

Figure 5:
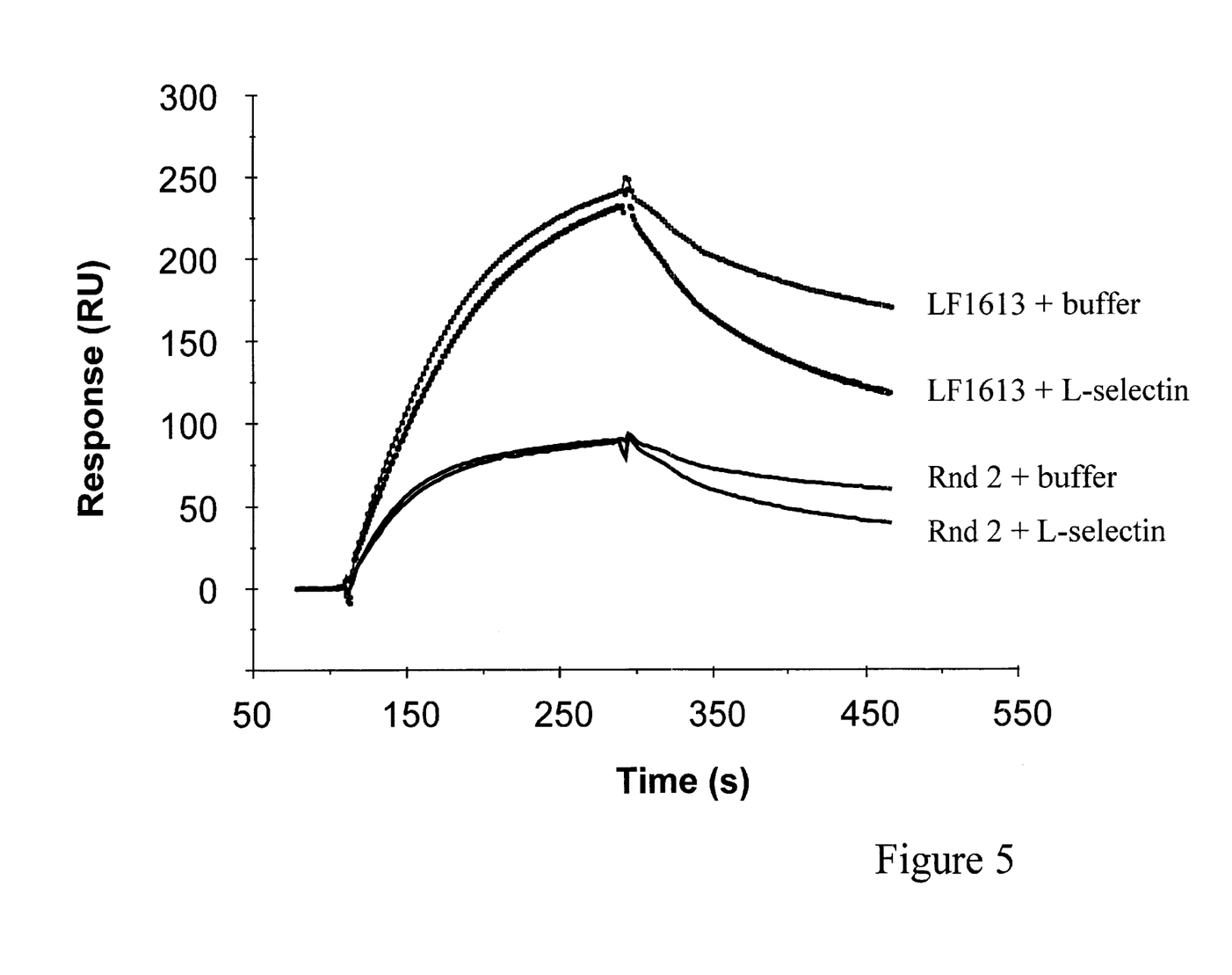
FIG. 5 shows the sensorgrams of LF1613 with and without soluble L-Selectin (500 nM) in the dissociation buffer.

Aliquots of the amplified pool of Round 2 were passed over a LS-Rg biosensor chip in SHMCK buffer at 37° C., and dissociated with buffer or with buffer containing soluble extracellular L-selectin (R+D Systems, Minneapolis, Minn.) at 500 nM (FIG. 5). The apparent off-rate is increased by almost 2 fold in the presence of excess soluble target (Table 3) which indicates that significant rebinding of the nucleic acids was occurring during dissociation in buffer. LF1613 also displays rebinding during the dissociation phase.

Aliquots were also applied and dissociated with buffer at varying flow rates (Table 3). The apparent off-rates are increased with increasing flow rates which indicates that rebinding is reduced with increased flow rates. The dissociated molecules with smaller ka's flow to waste before being able to rebind.

These preliminary experiments demonstrate that apparent off-rates can be manipulated by dissociation flow rate and by the presence of soluble target in the dissociation buffer. These manipulations greatly reduce rebinding and allow for partitioning of the remaining bound nucleic acids, some of which are expected to have slower off-rates.

In Example 2 we selected for molecules with faster on-rates with each round while not affecting off-rates. In Example 3, we demonstrate the conditions under which we could select for slow off-rates. The combination of these conditions should allow the selection of molecules with fast on-rates and slow off-rates in the same SELEX allowing for molecules with even better affinity.

TABLE 3

Rebinding of Oligo during Dissociation

| Oligo / Dissociation Parameter | kd, s-1 | Fold Reduction in kd |
|---|---|---|
| LF1613 / SHMCK's Buffer | 1.870E-03 | 1 |
| LF1613 / sol L-selectin | 3.020E-03 | 1.6 |
| SELEX 3-2 / SHMCK's Buffer | 1.510E-03 | 1 |
| SELEX 3-2 / sol L-selectin | 2.920E-03 | 1.9 |
| SELEX 3-2 / Flow 2 ul/min | 8.100E-04 | 0.5 |
| SELEX 3-2 / Flow 3 ul/min | 9.800E-04 | 0.6 |
| SELEX 3-2 / Flow 10 ul/min | 1.700E-03 | 1 |
| SELEX 3-2 / Flow 100 ul/min | 2.300E-03 | 1.4 |

We claim:

1. A method for identifying a nucleic acid ligand to a target from a candidate mixture of nucleic acids comprising
  a) immobilizing a target on a sensor chip;
  b) preparing a candidate mixture of nucleic acids;
  c) passing the candidate mixture of nucleic acids over the surface of the sensor chip, wherein nucleic acids having increased affinity to the immobilized target relative to the candidate mixture bind to the immobilized target;
  d) passing a wash buffer over the sensor chip at a determined flow rate to remove unbound nucleic acids;
  e) passing an eluent over the sensor chip to elute the nucleic acids which are bound to the immobilized target; and
  f) amplifying the eluted nucleic acids to yield a ligand-enriched mixture of nucleic acids, whereby a nucleic acid ligand to a target is identified.

2. The method of claim 1 further comprising g) repeating steps c), d), e) and f).

3. The method of claim 1 wherein the flow rate of the candidate mixture over the sensor chip is adjusted to optimize for the selection of nucleic acids having a fast on-rate and a slow off-rate.

4. The method of claim 3 wherein the flow rate of the wash buffer over the sensor chip is adjusted to optimize for the selection of nucleic acids having a fast on-rate and a slow off-rate.

5. The method of claim 1 wherein the composition of the wash buffer in step d) is adjusted to optimize for the selection of nucleic acids having a slow off-rate.

6. The method of claim 5 wherein the composition of said eluent comprises solubilized form of the immobilized target, wherein nucleic acids bound to the immobilized target having fast off-rates bind to the soluble target, wherein the selection for nucleic acids bound to the immobilized target having slow off-rates is enhanced.

7. The method of claim 1 wherein said candidate mixture of nucleic acids comprises single-stranded nucleic acids.

8. The method of claim 7 wherein said single stranded nucleic acids are ribonucleic acids.

9. The method of claim 7 wherein said single stranded nucleic acids are deoxyribonucleic acids.

10. The method of claim 8 wherein said candidate mixture of nucleic acids comprises 2'-modified ribonucleic acids.

11. The method of claim 8 wherein said 2'-modified ribonucleic acids comprise 2'-fluoro (2'-F) modified nucleic acids.

12. A method for identifying a nucleic acid ligand to a target from a candidate mixture of nucleic acids comprising:
   a) immobilizing a target on a sensor chip;
   b) preparing a candidate mixture of nucleic acids;
   c) dividing said candidate mixture into a plurality of aliquots;
   d) passing a first aliquot over the surface of the sensor chip, wherein nucleic acids having increased affinity to the immobilized target relative to the candidate mixture are bound to the immobilized target;
   e) passing a wash buffer over the sensor chip to remove unbound nucleic acids;
   f) repeating steps d) and e) until all of the aliquots have been injected;
   g) passing an eluent over the sensor chip at a determined flow rate to elute the nucleic acids which are bound to the immobilized target; and
   h) amplifying the eluted nucleic acids to yield a ligand-enriched mixture of nucleic acids, whereby a nucleic acid ligand to a target is identified.

13. A method for identifying a nucleic acid ligand to a target from a candidate mixture of nucleic acids comprising:
   a) immobilizing a target on a sensor chip;
   b) preparing a candidate mixture of nucleic acids;
   c) dividing said candidate mixture into a plurality of aliquots;
   d) passing a first aliquot over the surface of the sensor chip in a controlled flow, wherein nucleic acids having increased affinity to the immobilized target relative to the candidate mixture are bound to the immobilized target;
   e) washing the sensor chip with a buffer to remove unbound nucleic acids;
   f) eluting the nucleic acids which are bound to the immobilized target;
   g) repeating steps d), e), and f) until all of the aliquots of the candidate mixture have been injected;
   h) combining the eluted nucleic acids from step f); and
   i) amplifying the combined eluted nucleic acids to yield a ligand-enriched mixture of nucleic acids, whereby a nucleic acid ligand to a target molecule is identified.

* * * * *